(12) United States Patent
Scagliarini

(10) Patent No.: US 6,357,600 B1
(45) Date of Patent: Mar. 19, 2002

(54) DRIP CHAMBER FOR TRANSFUSION DIALYSIS INFUSION KITS AND THE LIKE

(75) Inventor: Massimo Scagliarini, Bologna (IT)

(73) Assignee: GVS S.r.l., Zola Predosa (IT)

(*) Notice: Subject to any disclaimer, the term of this patent is extended or adjusted under 35 U.S.C. 154(b) by 0 days.

(21) Appl. No.: 09/351,005

(22) Filed: Jul. 12, 1999

(30) Foreign Application Priority Data

Jul. 17, 1998 (IT) .......................... BO98A0442

(51) Int. Cl.[7] .......................... B01D 29/00; B01D 27/00
(52) U.S. Cl. .......................... 210/451; 210/448; 210/450; 210/453; 210/454
(58) Field of Search .......................... 210/436, 472, 210/435, 451, 453, 454, 441, 442, 447, 448, 477, 450; 604/251, 252

(56) References Cited

U.S. PATENT DOCUMENTS

| | | | | |
|---|---|---|---|---|
| 3,317,043 A | * | 5/1967 | Vanderpoel .................. | 210/94 |
| 4,169,795 A | * | 10/1979 | Raines ....................... | 210/446 |
| 4,173,223 A | * | 11/1979 | Raines et al. | |
| 4,283,289 A | * | 8/1981 | Meyst et al. ................ | 210/448 |
| 4,284,505 A | * | 8/1981 | Pope, Jr. et al. ............. | 210/448 |
| 4,400,277 A | * | 8/1983 | Leason ....................... | 210/441 |
| 4,601,820 A | | 7/1986 | Leason ....................... | 210/94 |
| 5,098,407 A | * | 3/1992 | Okamura .................... | 604/405 |

FOREIGN PATENT DOCUMENTS

EP        0788824        8/1997

* cited by examiner

*Primary Examiner*—John Kim
(74) *Attorney, Agent, or Firm*—Guido Modiano; Albert Josif; Daniel J. O'Byrne

(57) ABSTRACT

A drip chamber (1) for body fluid and discharge kits, includes a hollow tubular external closure (2) with a connector (4,5,6) formed at a first end for an outward fluid-flow connection to an external circuit and a second open end (3) arranged opposite to the first end, and a monolithic filtering element (7), formed of a cylindrical filtering body (8) with a first end supported by the connector bottom (4), and of a plug (10) with an inward fluid flow tube (11) monolithically attached to a second end of the cylindrical filtering body (8) and hermetically attached to the second end (3) of the hollow tubular external closure (2).

6 Claims, 3 Drawing Sheets

DRIP CHAMBER FOR TRANSFUSION DIALYSIS INFUSION KITS AND THE LIKE

BACKGROUND OF THE INVENTION

The present invention relates to a drip chamber for transfusion, dialysis, infusion kits, and the like.

Several kinds of drip chamber are commercially known which are meant to be inserted along the circuit of single-use extracorporeal lines such as kits for transfusions, dialysis or the like in order to prevent the passage of any impurities contained in the fluids being conveyed. Conventional drip chambers are composed of a plurality of components, usually at least four, which are glued together so as to form a tubular external enclosure which contains a filtration mesh and is closed at its ends respectively by two plugs provided with a coupling for the tubes for the infeed and discharge of the body fluids and optionally for additional tubes for connection to other lines or instruments, such as for example an injection point or a pressure gauge. The fluid that arrives from the infeed tube passes through the filtration mesh before reaching the outlet. It has been ascertained that drip chambers of this type operate correctly, and considering that they are discarded after a single use, in mass production it is a primary goal to minimize the number of parts required to produce the end product and to simplify the assembly procedure and its complexity.

SUMMARY OF THE INVENTION

The aim of the present invention is to obviate the above drawbacks of prior art devices, i.e. to provide a drip chamber for transfusion, dialysis, infusion kits, and the like which can be assembled in a simple manner and uses the smallest possible number of parts.

Within the scope of this aim, an object of the present invention is to achieve the above aim with a drip chamber which is relatively easy to provide in practice, safe in use, effective in operation and relatively low in cost.

This aim, these objects and others are all achieved by the present drip chamber for transfusion, dialysis, infusion kits, and the like, characterized in that it comprises a tubular external enclosure in which a first end is closed by a connector provided with at least one tube for connection to the external circuit and a second end lies opposite said first end, said enclosure accommodating a filtering element which is composed of a substantially cylindrical filtering body which forms an interspace with said enclosure, said filtering body having an end which is internal to said enclosure and is closed by a bottom and an end which is rigidly coupled to a closure element which is inserted in said second end of said enclosure and is provided with a tube for connection to the external circuit, said body and said closure element being monolithic.

BRIEF DESCRIPTION OF THE DRAWINGS

Further characteristics and advantages of the present invention will become apparent from the following detailed description of preferred embodiments of a drip chamber for kits for transfusion, dialysis, infusions and the like according to the invention, illustrated only by way of example in the accompanying drawings, wherein.

DESCRIPTION OF THE PREFERRED EMBODIMENTS

Figure 1:
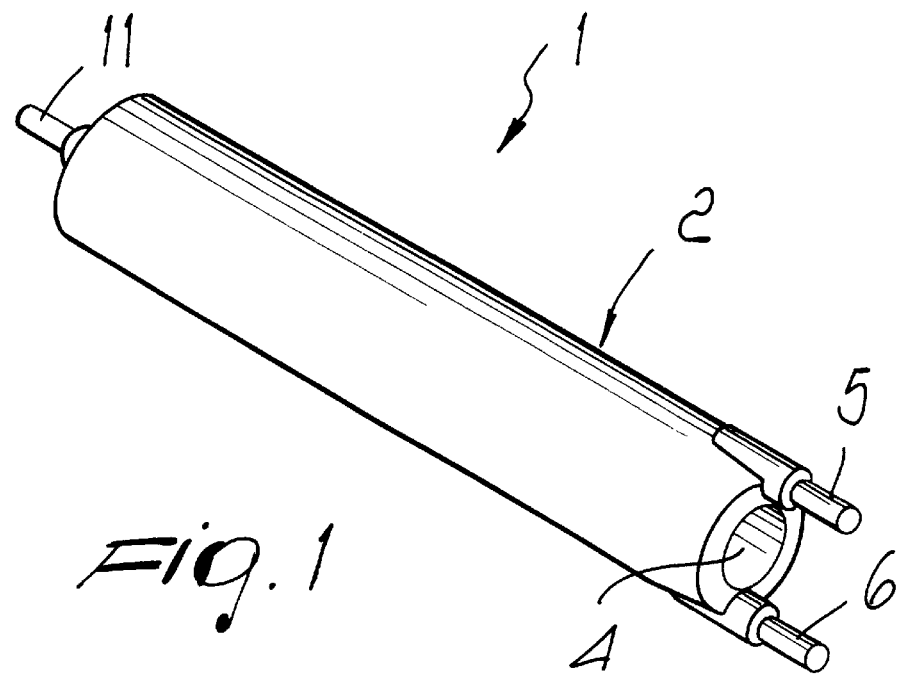
FIG. 1 is a perspective view of the chamber.

With reference to the above figures, 1 generally designates a drip chamber for kits for transfusion, dialysis and the like according to the invention.

The drip chamber 1 is composed of a tubular external enclosure 2 which is formed by molding a material such as plastics, so as to have an open end 3 and another end which is closed by a connector which comprises a bottom 4 from which two tubes 5 and 6 protrude, which are parallel to the axis of the enclosure, and are designed for connection to a tube which leads to the pressure gauge or to the injection point and respectively to a tube for the discharge of the blood or other medical liquid.

The numeral 7 designates a filtering element which is formed by a filtering cylinder 8 which is formed by a filtering mesh and whose diameter is slightly smaller than the diameter of the enclosure 2, so that when it is inserted in said enclosure it defines an interspace 9 between the enclosure and the cylinder 8. The end of the element 7, arranged at the opening 3, forms a plug 10 which is provided with an annular outer lip for abutment on the edge of the enclosure 2 and is centrally provided with a tube 11 which protrudes axially outward and connects the inside of the filtering cylinder 8 to the outside; the hermetic closure of the plug 10 in the enclosure 2 is achieved by gluing, welding or mechanical interlocking of the components.

The tube 11 is designed for coupling to the infeed tube for the blood or other medical liquid from the external circuit.

In order to use the chamber 1, the connecting tubes can be constituted by cannula-type perforating tips adapted to perforate bottles and flasks with a rubber stopper or pouches containing blood or other medical liquids.

The opposite end of the element 7 rests on the bottom 4 and is provided with a collar 13 for centering the filtering element inserted on the edge of the bottom 4.

A fundamental feature of the invention is the particular structure of the filtering element 7, which allows to form the filtering cylinder 8, the collar 13, the plug 10 and the tube 11 monolithically by molding plastics.

The operation of this device is known: the blood (or other liquid) conveyed by the tube 11 enters the filtering cylinder 8, flows from there into the interspace 9 and then exits through the tube 6. Conveniently, the path of the fluid can be reversed without affecting in any way the function of the instrument.

The tube 5 is connected to a pressure gauge, which measures the blood pressure by measuring the pressure of the air that is present in the upper half of the filter, and a hydrophobic membrane 12 is inserted therein; said membrane is designed to prevent any rise of the blood along the tube 5 to the pressure gauge while allowing the passage of air and therefore the measurement of the pressure.

The drip chamber provided according to the invention is formed by just two parts and its assembly is extremely simple: it is in fact sufficient to glue, weld or interlock the centering collar 13 and the plug 10 to the external enclosure 2.

Figure 3:
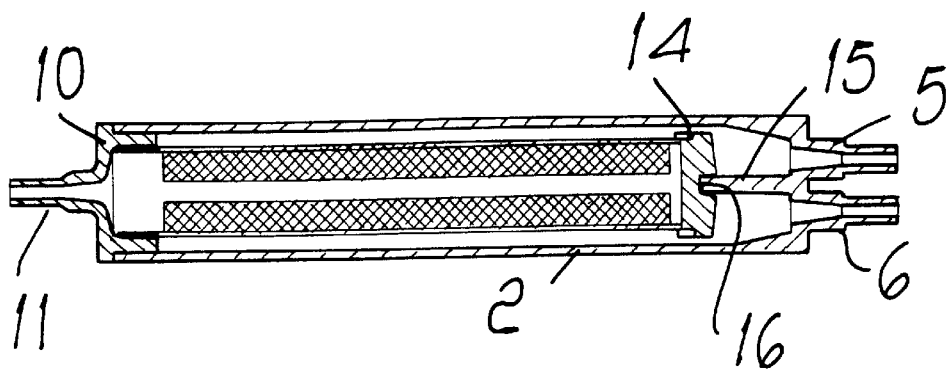
FIG. 3 is a sectional view of a first variation.

In an alternative embodiment of the filter, shown in FIG. 3, the filtering element 7 is closed, on the side of the tubes 5 and 6, by a bottom 14 which is inserted snugly in the end of the filtering cylinder 8. A finger 15 protrudes axially from the region between the tubes 5 and 6 towards the inside of said enclosure and abuts in a central seat 16 formed in the bottom 14, preventing it from leaving the cylinder 8 and allowing to center it inside the enclosure 2.

Figure 4:
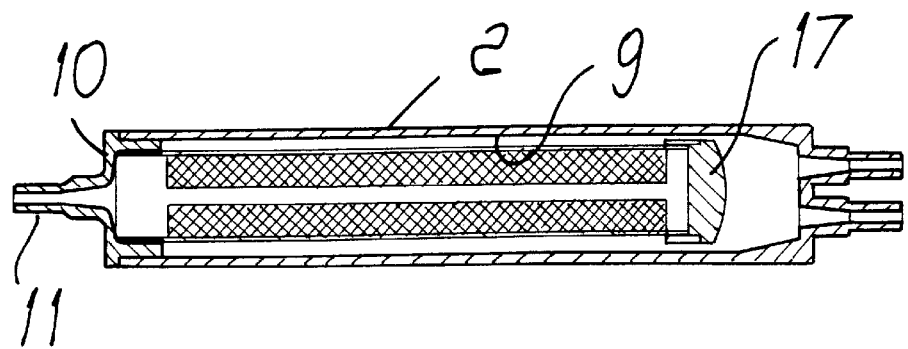
FIG. 4 is a sectional view of a second variation.

A further embodiment of the invention, shown in FIG. 4, is constituted by an external enclosure 2 which contains a filtering cylinder, closed as in the preceding example by means of a bottom 17, which in this case is glued to the mouth of the cylinder 8 and has a plurality of radial spacers which are adapted for centering by resting on the internal surface of the enclosure 2.

Figure 5:
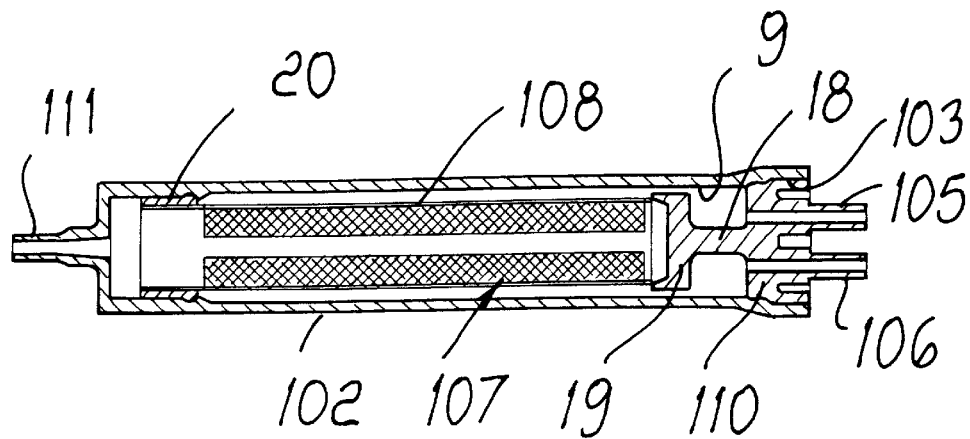
FIG. 5 is a sectional view of a third variation.
Figure 2:
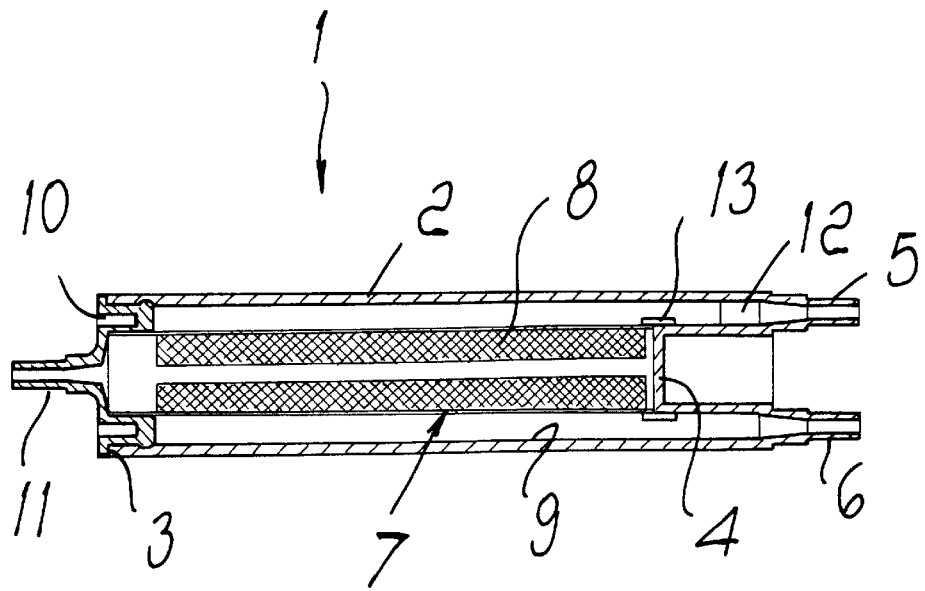
FIG. 2 is a longitudinal sectional view of the chamber of FIG. 1.

In still another embodiment of the chamber 1 (see FIG. 5), the open end of the external enclosure 102 is located on the liquid discharge side instead of on the infeed side as in the preceding example. In this case, the filtering element 107 is composed of a plug 110 which is shaped so as to be able to close hermetically the opening 103 of the enclosure 102. Two tubes 105 and 106 protrude outwards from the plug and are meant respectively for connection to the pressure gauge and to the liquid discharge tube; a finger 18 protrudes inwards from said plug and ends by forming a bottom 19 for closing the filtering cylinder 108. The open end of the cylinder 108 forms a tubular portion 20 adapted to form a seal with the internal wall of the enclosure 2, so as to force the liquid that enters through the tube 111 to pass through the filtering walls of the cylinder 108 in order to reach the interspace 9 and from there the discharge connector. The finger 18 can be folded and compressed so as to define a sort of leaf spring adapted to apply pressure toward the cylinder 108 in order to ensure the seal between said cylinder and the wall of the enclosure 102.

Figure 6:
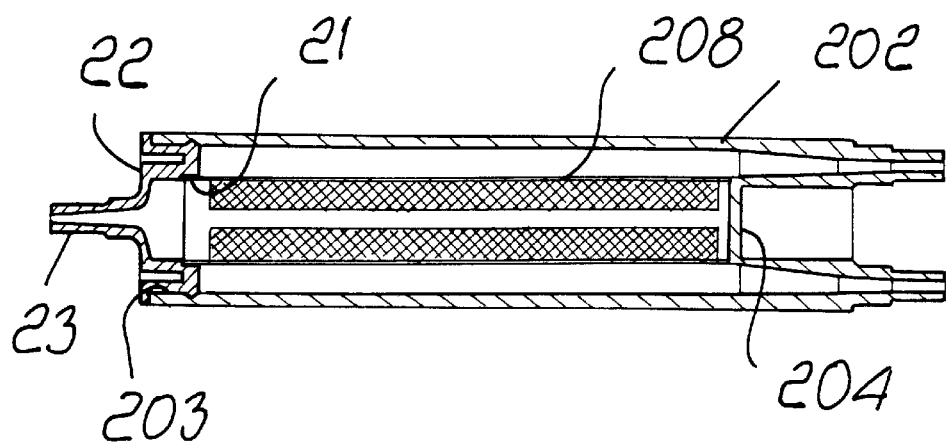
FIG. 6 is a sectional view of a fourth variation.

Furthermore, in still another alternative solution, shown in FIG. 6, the cylinder 208 and the external enclosure 202 are provided monolithically. In this case, the seal between the bottom 204 of the enclosure 202 and the end of the cylinder is provided during molding, while the opposite end is provided with a tubular portion 21 adapted to hermetically engage the plug 22, which closes the opening 203 and has a coupling 23 for connection to the infeed tube.

Figure 7:
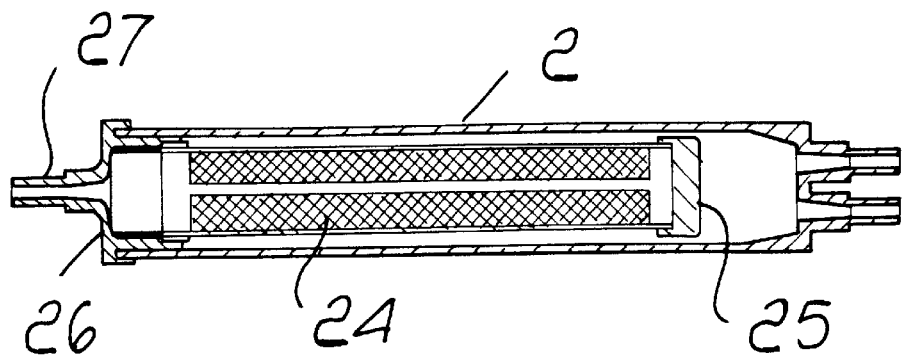
FIG. 7 is a sectional view of a fifth variation.

In a last embodiment proposed by way of example in FIG. 7, the filtering element is constituted, according to the known art, by a cylinder 24 in which the lateral walls are formed by a filtering mesh; said cylinder is closed at one end by a bottom 25 and is glued or inserted by pressing, at the other end, in a plug 26 for closing the open side of the external enclosure 2. The plug 26 is axially provided with a tube 27 for connection to the fluid infeed tube.

It has thus been observed that the invention achieves the intended aim and object and that in particular it is formed with a minimal number of parts, two or three at the most), which can be manufactured easily and are simple to assemble.

The invention thus conceived is susceptible of numerous modifications and variations, all of which are within the scope of the inventive concept; all the details may furthermore be replaced with other technically equivalent ones. In particular, the connectors for the discharge of the liquid can also be more than two and can comprise, for example, an injection point for adding substances to the filtered liquid.

In practice, the materials employed, as well as the shapes and the dimensions, may be any according to requirements without thereby abandoning the scope of the protection of the appended claims.

What is claimed is:

1. A drip chamber for body fluid and discharge kits, comprising: a tubular external enclosure having opposite first and second ends thereof; a connector closing the first end of the external closure; at least one tube provided at said connector for connection to an external circuit; a filtering element accommodated in said enclosure; said filtering body being composed of a substantially cylindrical filtering body which forms an interspace with said enclosure, said filtering body having a first end which is internal to said enclosure and a second end; a bottom element for closing said fist end of the filtering body; a closure element being rigidly coupled to said second end of said filtering body, said closure element being further inserted in said second end of said enclosure; a tube provided at said closure element for connection to the external circuit, said filtering body and said closure element being provided as a monolithic structure; a collar-shaped portion which is formed at the first internal end of said filtering body, said first internal end of said filtering element being closed by said bottom element which is inserted in said collar-shaped portion; and a finger which is rigidly coupled to said connector, said bottom element being retained in closed position by said connector.

2. The chamber of claim 1, wherein said bottom element is monolithic with said connector.

3. The chamber of claim 1, wherein said closure element is constituted by a plug provided with an external annular lip abutting against an edge region of said enclosure.

4. The chamber of claim 1, wherein said bottom being monolithic with said connector and said filtering body.

5. A drip chamber for body fluid discharge kits, comprising:

a hollow tubular external closure, said hollow tubular external closure comprising a connector formed at a fist end of said hollow tubular external closure, said connector having at least one outlet tube for an outward fluid-flow connection to an external circuit, said hollow tubular external closure also comprising a second end which is open and arranged opposite to said first end;

a monolithic filtering element, said monolithic filtering element comprising a cylindrical filtering body having a first end and a second end, said monolithic filtering element further comprising a plug monolithically attached to said second end of said cylindrical filtering body, said plug comprising an inlet tube for an inward fluid-flow connection to said external circuit, and said monolithic filtering element being inserted into and connected wit said hollow tubular external closure such that said first end of said cylindrical filtering body is arranged internally of said hollow tubular external closure and said plug is hermetically attached to said second end of said hollow tubular external closure;

said first end of said cylindrical filtering body being supported by a bottom element of said connector formed at said first end of said hollow tubular external closure, said bottom element of said connector being cylindrical and said monolithic filtering element further comprising a collar attached to said first end of said cylindrical filtering body and arranged about said bottom element.

6. A drip chamber for body fluid and discharge kits, comprising:

a hollow tubular external closure, said hollow tabular external closure comprising a connector formed at a first end of said hollow tubular closure, said connector having at least one outlet tube for an outward fluid-flow connection to an external circuit, said hollow tubular external closure also comprising a second end which is open and arranged opposite to said first end;

a monolithic filtering element, said monolithic filtering element comprising a cylindrical filtering body having a first end and a second end, said monolithic filtering element further comprising a plug monolithically attached to said second end of said cylindrical filtering body, said plug comprising an inlet tube for an inward fluid-flow connection to said external circuit, and said monolithic filtering element be inserted into and connected with said hollow tubular external closure such that said first end of said cylindrical filtering body is arranged internally of said hollow tabular external closure and said plug is hermetically attach to said second end of said hollow tubular external closure;

said first end of said cylindrical filtering body being supported by a bottom element of said connector formed at said first end of said hollow tubular external closure, said bottom element of said connector comprising an axially protruding finger which abuts in a central seat of a bottom of said first end of said cylindrical filtering body.

* * * * *